United States Patent [19]

Martin

[11] Patent Number: 4,627,441
[45] Date of Patent: Dec. 9, 1986

[54] B MEDICAL MONITORING CIRCUIT

[75] Inventor: Eric A. Martin, St. Anthony, Minn.

[73] Assignee: Medtronic, Inc., Minneapolis, Minn.

[21] Appl. No.: 795,553

[22] Filed: Nov. 6, 1985

Related U.S. Application Data

[63] Continuation of Ser. No. 604,797, Apr. 27, 1984.

[51] Int. Cl.[4] ............................................. A61B 5/04
[52] U.S. Cl. ....................................... 128/696; 128/901
[58] Field of Search ........................... 128/421–422, 128/419 R, 696–697, 901–902

[56] References Cited

U.S. PATENT DOCUMENTS

| | | | |
|---|---|---|---|
| 4,161,945 | 7/1979 | Grossman | 128/696 |
| 4,194,511 | 3/1980 | Feldman | 128/696 |
| 4,211,237 | 7/1980 | Nagel | 128/698 |
| 4,324,253 | 4/1982 | Greene et al. | 128/421 |
| 4,331,157 | 5/1982 | Keller, Jr. et al. | 128/419 R |

FOREIGN PATENT DOCUMENTS

| | | | |
|---|---|---|---|
| 2926165 | 1/1980 | Fed. Rep. of Germany | 128/902 |
| 135685 | 5/1979 | German Democratic Rep. | 128/697 |

Primary Examiner—William E. Kamm
Assistant Examiner—Mitchell J. Shein
Attorney, Agent, or Firm—Reed A. Duthler; Joseph F. Breimayer; John L. Rooney

[57] ABSTRACT

A monitoring circuit for use in conjunction with an electrical stimulator and an electrical monitor, such as an EKG monitor, having a differential amplifier input. The circuit functions by equalizing the electrical signals due to the stimulator on both inputs of the electrophysiological monitoring device. Because the stimulator induced signals appear at equal levels on both inputs, the differential amplifier of the monitoring device will cancel them out, allowing display of the underlying physiological signals.

4 Claims, 3 Drawing Figures

B MEDICAL MONITORING CIRCUIT

This is a continuation of co-pending application Ser. No. 604,797 filed on Apr. 27, 1984.

BACKGROUND OF THE INVENTION

1. Field of the Invention

The present invention relates to devices for filtering electrical stimultion interference from physiologic monitoring devices.

2. Prior Art

Electrical stimulation is well accepted as a means of pain control. Stimulation is provided either externally through transcutaneous electrical nerve stimulation (TENS) or internally through implanted devices such as spinal cord stimulators.

There are many situations in which this method of pain relief is not available because it would interfere with electrical signals being sensed on the body. In these situations, the patient must resort to less desirable pain control means, such as drug therapy.

For example, one situation in which TENS is used to control pain is during post-operative recovery. In this situation, there is often constant EKG monitoring of the patient. TENS cannot be used while EKG is being monitored, since the TENS interference will distort the EKG signal.

EKG devices reject noise which is common to both leads. In TENS, however, the TENS stimulation signal will appear at different levels on the two leads through which the EKG is being sensed. Therefore, a distorted signal will be displayed on the EKG monitor.

There have been various attempts to use TENS while monitoring patients. In U.S. Pat. No. 4,161,945 to Grossman, a selective interference filter is employed. This involves band rejection or a notch filter to filter the bandwidth in which TENS stimulation would normally occur. This necessarily distorts the signal in that the bandwidth which is filtered must be altered in the EKG signal.

U.S. Pat. No. 4,331,157 to Keller, Jr. et al, discloses apparatus for temporarily holding EKG signals at such time as TENS stimulation is occurring. Therefore, the two can coexist, although not stimultaneously.

These prior art attempts fail to allow simultaneous stimulation and monitoring, without degrading the monitored signal.

SUMMARY OF THE INVENTION

Apparatus constructed according to the present invention samples the stimulation signal produced by a TENS device or other electrical stimulator. The apparatus determines the difference between the two leads of the stimulating device and preferably inverts the signal. The sample signal is then added to one lead of a monitoring device, such as an EKG system. The added signal is attenuated to provide the same level of stimulation signal on each referant lead (not the reference ground lead) of the monitoring device. The monitoring device will then reject the noise common to both leads. The sense signal, such as an EKG signal, can then be protrayed accurately on a monitor.

A medical monitoring filter includes means for sensing an electrical stimulation signal being provided to a patient and means for adding the stimulation signal to an electrical signal representative of an electrical physiologic parameter of a patient.

DETAILED DESCRIPTION OF THE PREFERRED EMBODIMENT

Figure 1:
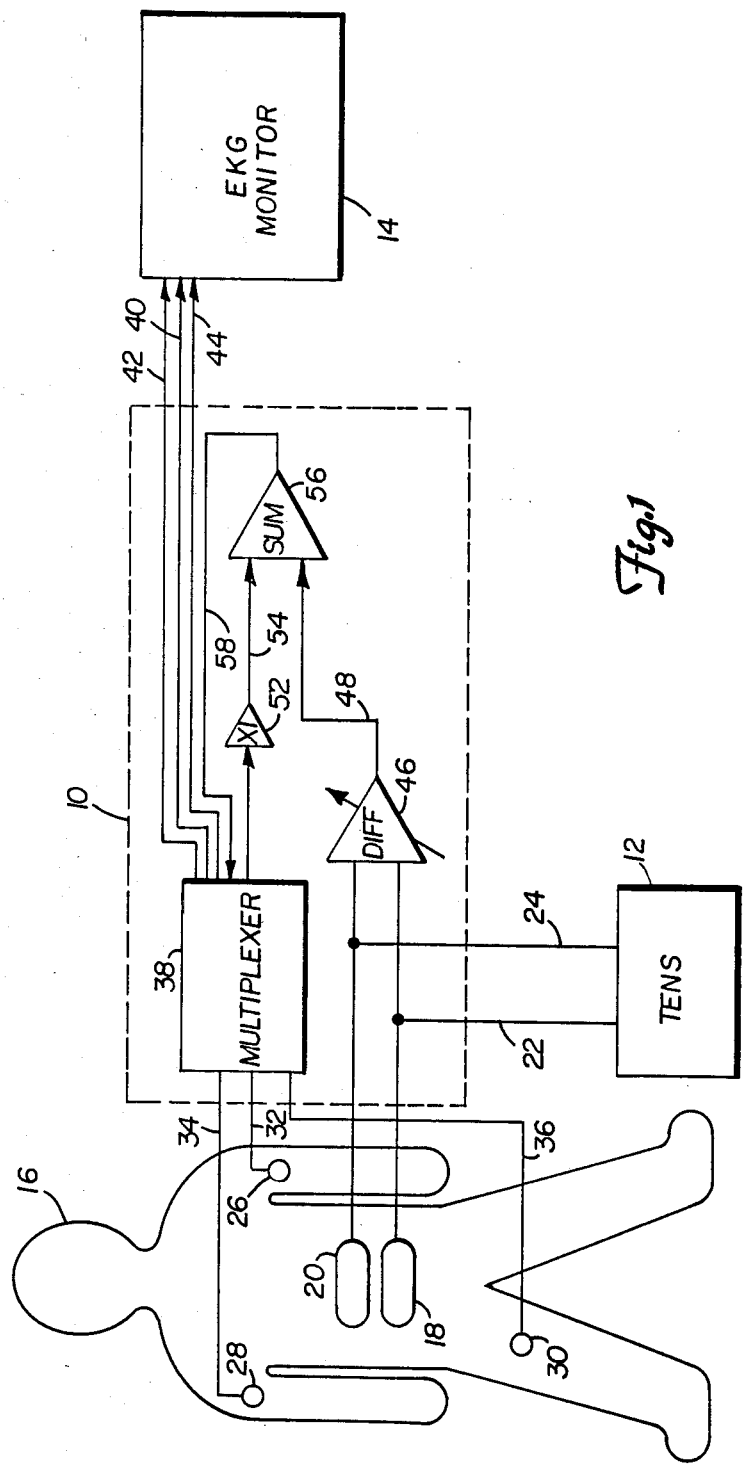
FIG. 1 is a block diagram depiction of the present invention shown in relation to a patient in schematic form.

In FIG. 1, a filter 10, constructed according to the present invention, is shown in use in conjunction with an electrical stimulation of TENS unit 12 and a physiologic monitor 14, which in this case is an EKG monitor. The TENS unit and EKG monitor are merely illustrative. A filter constructed according to the present invention may be employed with any type of electrical stimulator and physiologic electrical monitor.

A patient 16 is shown receiving electrical stimulation from electrodes 18 and 20 which are electrically connected to TENS unit 12 by lead wires 22 and 24 respectively. In FIG. 1, electrodes 18 and 20 are schematically shown as post-operative electrodes, but may be of any of the many types of stimulation electrodes.

Also affixed to patient 16 are three sensing electrodes: left arm electrode 26, right arm electrode 28, and right leg electrode 30. In the example illustrated, electrodes 26 through 30 are sensing electrodes which convey signals through leads 32, 34 and 36 respectively.

Within filter 10 is a multiplexer 38 which receives input from leads 32 through 36. Output from filter 10 including the sensed EKG signals on leads 32 through 36 is conducted from multiplexer 38 to EKG monitor 14 on leads 40, 42 and 44, respectively.

Within filter 10, the electrical stimulation signal on leads 22 and 24 is sensed by differential amplifier 46. Differential amplifier 46 determines a difference signal which is transmitted on line 48. In the preferred embodiment, the stimulation signal is inverted by differential amplifier 56 before transmission on line 48. Thus filter 10 acts as a subtractive filter.

In normal physiologic monitoring, such as on EKG, two leads are used to sense a potential difference across a portion of the patient's body. In filter 10, input from one lead is passed on line 50 to amplifier 52 which amplifies the signal and passes along line 54 to summing amplifier 56. Summing amplifier 56 adds the difference signal on line 48 to the EKG signal on line 54 and returns the summed signal on line 58 to multiplexer 38. The summed signal from line 58 is then relayed to EKG monitor 14 as a normal EKG signal. Therefore, the signal from TENS unit 12 has been added (preferably adding a negative signal to effectively subtract) to one EKG lead so that the TENS interference on that lead is identical to TENS interference on the other EKG lead in use. The common interference is then discarded by EKG monitor 14.

Figure 2A:
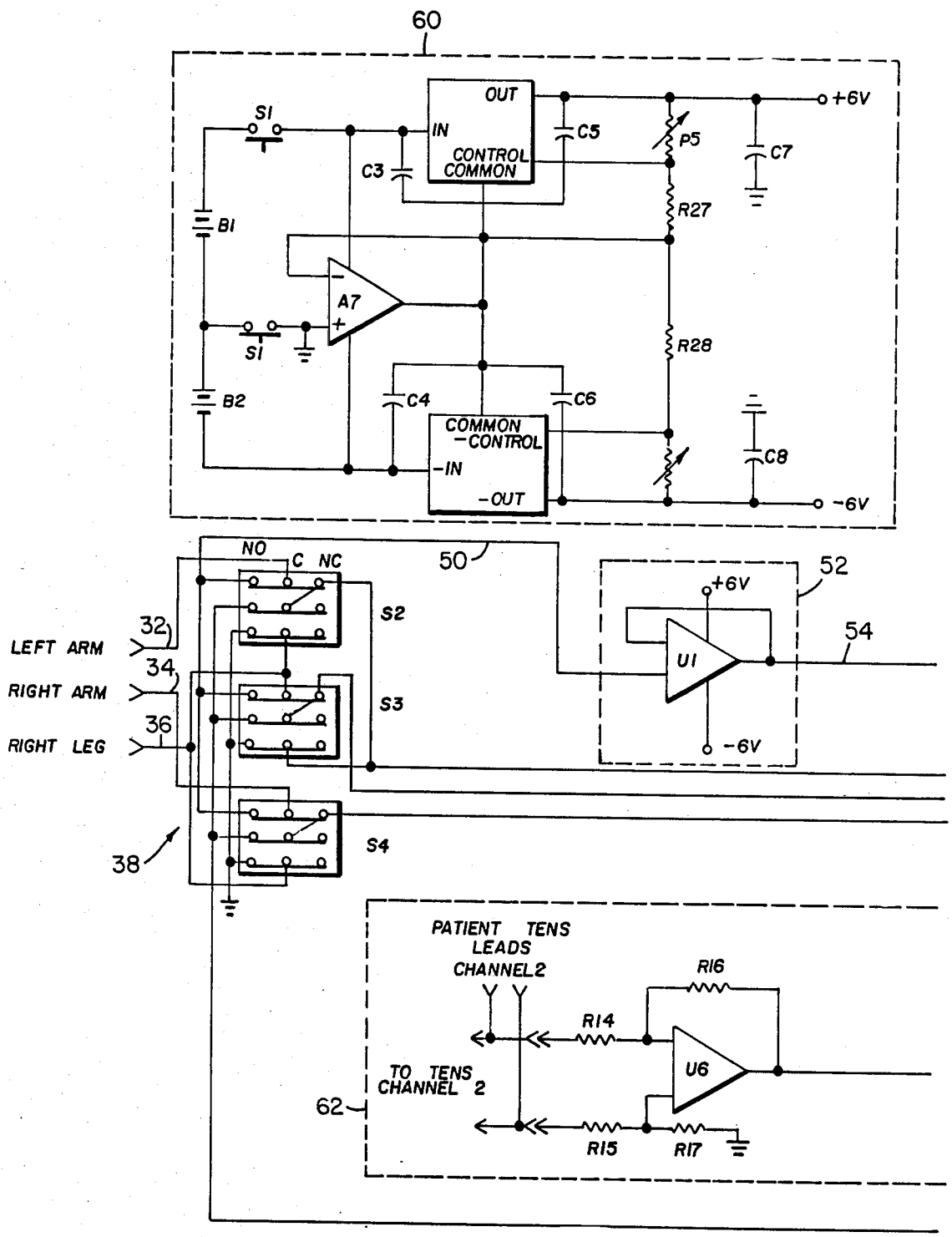
FIGS. 2a and 2b in combination are a schematic representation of the circuitry of the invention as shown in the block diagram of FIG. 1.
Figure 2B:
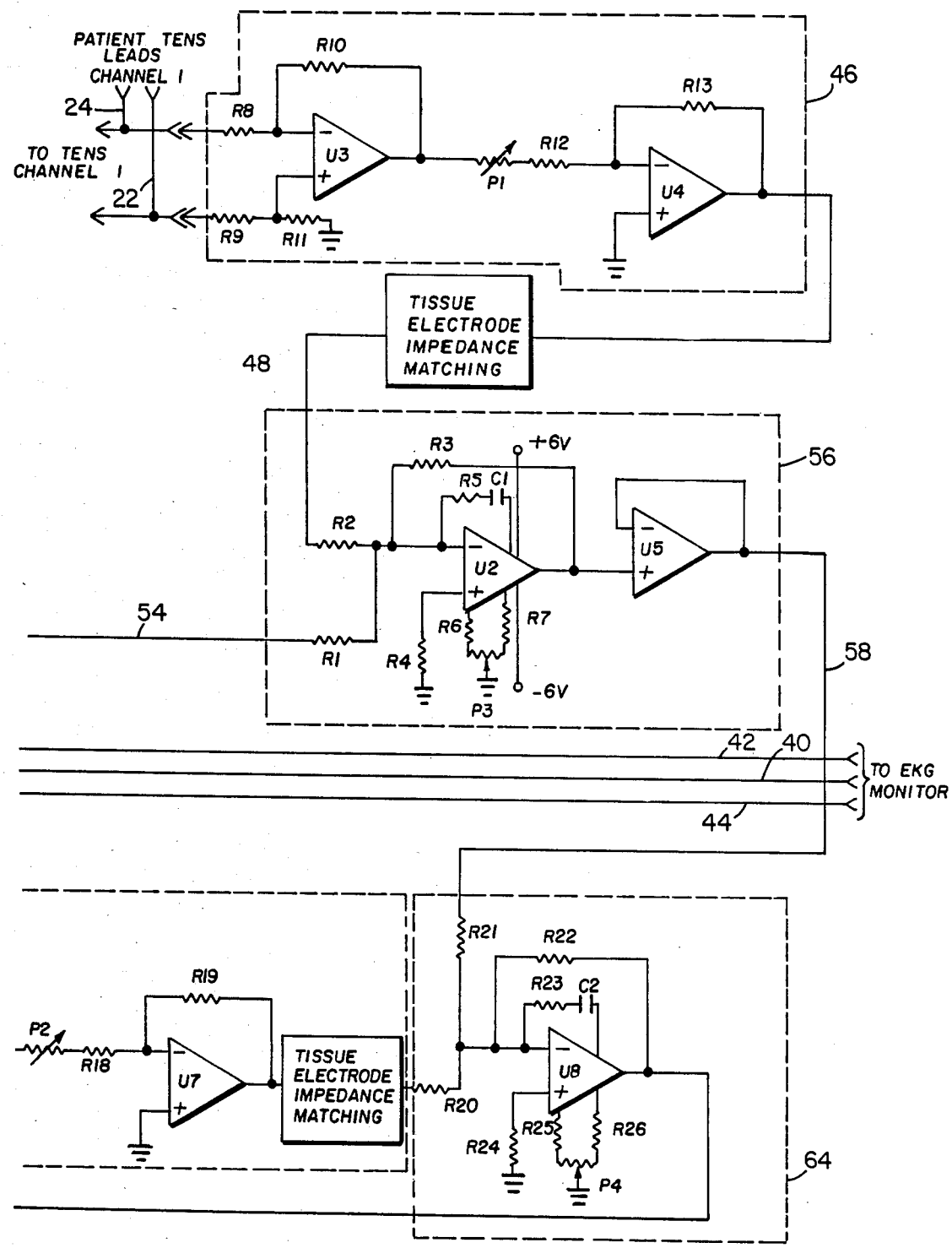

Filter 10 of FIG. 1 is shown in detail in the schematic of FIGS. 2a and 2b. Power source 60 forms no part of the present invention and is disclosed to show the power used in the illustrated embodiment. Any power source which can provide constant plus six volt and minus six volt power is suitable for use in the filter of the present invention.

The schematic illustrates a two-channel TENS device. For simplicity of description, only one channel is described.

The embodiment of multiplexer 38 shown in FIG. 2a is a series of switches S2, S3, and S4 which are used to select any two of the three EKG leads 32, 34 and 36. As discussed above in relation to FIG. 1, a signal from one EKG lead is transmitted along line 50 to amplifier 52 which contains operational amplifier U1. Amplifier U1 provides isolation of the circuitry from leads 32 through 36. The signal is relayed along line 54 to summing amplifier 56.

Operational amplifier U3 and its associated resistors provide high input impedance difference amplification to obtain a sample of TENS leads 22 and 24, which will not affect stimulation intensity. The sample is amplified and inverted by amplifier U4 and its associated resistors. This difference signal is variably attenuated by variable resistor P1. P1 is an operator control which is adjusted by the technician or nurse to get the proper gain on one EKG line to match the signal on the other EKG line for the particular patient electrode placement or patient tissue impedance. This signal is then relayed through amplifier U4 to circuitry for tissue electrode impedance matching.

The box marked "Tissue Electrode Impedance Matching" represents standard circuitry to represent the electrode/skin interface. It is common in the science of pain control to model this interface as a leaky capacitor in series with a resistor network. Such a capacitor/resistor network may be used in conjunction with the present invention to more finely tune the filter 10.

The two signals on line 48 and line 54 are summed by operational amp U2 to remove the TENS artifact. The sum is then amplified by unity gain amplifier U5 which provides isolation from feedback between summing amplifiers. The summed signal is then relayed on line 58.

In the embodiment illustrated, the TENS device uses two channels for stimulation. Therefore, circuitry 62 is included with operates in identical manner to differential amplifier 46. A second summing amplifier 64 sums the signal on line 58 with that produced by inverting differential amplifier 62. The result is transmitted to multiplexer 38 for relay on one of EKG lines 40, 42 or 44. Second differential amplifier 62 and second summing amplifier 64 work in a manner identical to the first channel so are not described here.

Using a filter constructed according to the present invention involves simply connecting the filter to the TENS stimulation leads and to the EKG leads and monitor. As in normal EKG operation, two EKG leads are chosen for sensing. One lead is chosen for filtering. The operator then adjusts the variable resistor P1 through a switch to equalize the interference of a TENS signal on each of the two EKG leads. As a standard in EKG monitors, the common interference is discarded and the EKG signal is protrayed without TENS interference.

The following component values were used in the illustrated embodiment:

| Capacitors (microfarads) | | | |
|---|---|---|---|
| C1 | 0.1 | C5 | 0.1 |
| C2 | 0.1 | C6 | 1.0 |
| C3 | 0.33 | C7 | 2.2 |
| C4 | 2.0 | C8 | 2.2 |
| Resistors (KOhms) | | | |
| R1 | 1.8 | R14 | 1 |
| R2 | 1.8 | R15 | 1 |
| R3 | 1.8 | R16 | 1 |
| R4 | 1 | R17 | 1 |
| R5 | 3 | R18 | 5.6 |
| R6 | 27 | R19 | 1 |
| R7 | 27 | R20 | 1.8 |
| R8 | 1 | R21 | 1.8 |
| R9 | 1K | R22 | 1.8 |
| R10 | 1 | R23 | 3 |
| R11 | 1 | R24 | 1 |
| R12 | 5.6 | R25 | 27 |
| R13 | 1 | R26 | 27 |

Operational amplifiers U1, U3, U4, U6, and U7 are OP27 type amplifiers. Operational amplifiers U2, U5, and U8 are LM 318 type amplifiers.

Although the present invention has been described in terms of a two channel TENS unit and a standard EKG monitor, it is to be understood that it is equally applicable to other stimulation modes and other physiologic monitoring devices which may receive stimulation interference.

What is claimed is:

1. Medical monitoring circuit for use in conjunction with an electrical stimulator of the type which includes two stimulating electrodes which are attached to a human body and which provides an electrical output to said stimulating electrodes by which means an electrical potential difference is applied to said human body and for use with a monitoring device of the type which includes two monitor inputs and a monitor ground input, and which displays the potential difference between signals applied to the said two monitor inputs and for use in conjunction with first, second and third sensing electrodes coupled to said human body at three different locations, said monitoring circuit comprising:

circuit ground means for coupling to said third sensing electrode and for providing a reference ground;

first input means coupled to said circuit ground means for coupling to said first sensing electrode and for generating a first signal indicative of the electrical potential difference between said first sensing electrode and said circuit ground;

second input means coupled to said circuit ground means for coupling to said second sensing electrode and for generating a second signal indicative of the potential difference between said second sensing electrode and said circuit ground, whereby the electrical potential difference between said first and second signals is a result both of electrophysiological activity of said body and of said electrical potential difference applied by said stimulating electrodes;

third input means coupled to said circuit ground means for coupling to said electrical stimulator and responsive to the output of said electrical stimulator and for generating a third signal indicative of the electrical potential difference applied to said human body by said stimulating electrodes;

first output means coupled to said first input means for providing said first signal to one of said two monitor inputs of said monitoring device;

second output means coupled to said second and third input means for adding said third signal to said second signal and for providing the sum of said second and third signals to the other of said two monitor inputs of said monitoring device, said second output means including adjustment means for adjusting the amplitude of said third signal prior to adding said third signal to said second signal whereby said third signal may be appropriately adjusted such that the electrical potential difference between said second and third signals reflects only the electrophysiological activity of said human body; and third output means coupled to said circuit ground means, for coupling said circuit ground means to said monitor ground input.

2. A monitoring circuit according to claim 1 wherein said third input means comprises a differential amplifier.

3. A monitoring circuit according to claim 1 wherein said second output means comprises a summing amplifier.

4. A monitoring circuit according to claim 1 or claim 2 or claim 3 wherein said second output means comprises tissue electrode impedance matching circuitry means for simulating the attenuating and filtering effect of said human body on said potential difference applied to said human body by said stimulator, said tissue electrode impedance matching means coupled to said third input means and attenuating and filtering said third signal prior to addition of said third signal to said second signal by said second output means.

* * * * *